US011441123B2

(12) United States Patent
Iyoku et al.

(10) Patent No.: US 11,441,123 B2
(45) Date of Patent: Sep. 13, 2022

(54) METHOD FOR EVALUATING QUALITY OF HUMAN MESENCHYMAL STEM CELL, AND MONOCLONAL ANTIBODY FOR USE IN SAID METHOD (71) Applicant: PUREC CO., LTD., Izumo (JP)

(72) Inventors: Yumi Iyoku, Tokyo (JP); Hideyuki Okano, Tokyo (JP); Yo Mabuchi, Mizuho (JP)

(73) Assignee: PUREC CO., LTD., Izumo (JP)

( * ) Notice: Subject to any disclaimer, the term of this patent is extended or adjusted under 35 U.S.C. 154(b) by 0 days.

(21) Appl. No.: 17/190,192

(22) Filed: Mar. 2, 2021

(65) Prior Publication Data

US 2021/0230553 A1 Jul. 29, 2021

Related U.S. Application Data (63) Continuation of application No. 15/321,679, filed as application No. PCT/JP2015/071770 on Jul. 31, 2015, now abandoned.

(30) Foreign Application Priority Data

Aug. 1, 2014 (JP) ................. 2014-157367

(51) Int. Cl.
C12N 5/0775 (2010.01)
G01N 33/569 (2006.01)
C07K 16/28 (2006.01)
C12P 1/00 (2006.01)
C12N 15/02 (2006.01)
C12Q 1/04 (2006.01)
C12Q 1/6881 (2018.01)

(52) U.S. Cl.
CPC .......... C12N 5/0663 (2013.01); C07K 16/28 (2013.01); C12N 15/02 (2013.01); C12P 1/00 (2013.01); C12Q 1/04 (2013.01); C12Q 1/6881 (2013.01); C12Y 207/10001 (2013.01); G01N 33/56966 (2013.01); G01N 2333/705 (2013.01); G01N 2333/912 (2013.01)

(58) Field of Classification Search
None
See application file for complete search history.

(56) References Cited

U.S. PATENT DOCUMENTS

| 10,208,287 B2 | 2/2019 | Yamashita et al. |
| 2005/0148506 A1 | 7/2005 | Billiard et al. |
| 2007/0116701 A1 | 5/2007 | Gurney et al. |
| 2009/0047287 A1 | 2/2009 | Billiard et al. |
| 2010/0297089 A1 | 11/2010 | Oh |
| 2011/0053183 A1 | 3/2011 | Matsuzaki et al. |
| 2012/0087933 A1 | 4/2012 | Tom et al. |
| 2013/0209415 A1 | 8/2013 | Ardehali et al. |

FOREIGN PATENT DOCUMENTS

| JP | 2006/524508 A | 11/2006 |
| JP | 2009/60840 A | 3/2009 |
| JP | 2009/513708 A | 4/2009 |
| JP | 2009-527485 A | 7/2009 |
| JP | 2013-66414 A | 4/2013 |
| JP | 2015-43768 A | 3/2015 |

OTHER PUBLICATIONS

Dickinson et al., The Wnt5a Receptor, Receptor Tyrosine Kinase-Like Orphan Receptor 2, is a Predictive Cell Surface Marker of Human Mesenchymal Stem Cells with an Enhanced Capacity for Chondrogenic Differentiation. Stem Cells, 2017, 35:2280-2291 (Year: 2017).*
Anam et al. Comparative analysis of gene transcripts for cell signaling receptors in bone marrow-derived hematopoietic stem/progenitor cell and mesenchymal stromal cell populations (Stem Cell Res Ther, 2013, 4:112)(Year: 2013).
Ardehali et al., Prospective isolation of human embryonic stem cell-derived cardiovascular progenitors that integrate into human fetal heart tissue (PNAS, 2013, 111:3405-3410)(Year 2013).
Bolzoni et al., Myeloma cells inhibit non-canonical wnt co-receptor ror2 expression in human bone marrow osteoprogenitor cells: effect of wnt5a/ror2 pathway activation on the osteogenic differentiation impairment induced by myeloma cells, Leukemia (2013) 27, 451-463 (Year: 2013).
Cai et al., "Stable Genetic Alterations of b-Catenin and ROR2 Regulate the Wnt Pathway, Affect the Fate of MSCs," J. Cell. Physiol. (2014), vol. 229, pp. 791-800.
CGH array data, Gene Expression Omnibus (GEO) (accession No. GSE34484) (Dec. 22, 2011).
Dezawa et al., Bone Marrow Stromal Cells Generate Muscle Cells and Repair Muscle Degeneration, Science, Jul. 8, 2005;309(5732):314-7, (Year: 2005).
Dickinson et al., "The Wnt5a Receptor, Receptor Tyrosine Kinase-Like Orphan Receptor 2, is a Predictive Cell Surface Marker of Human Mesenchymal Stem Cells with an Enhanced Capacity . . . ," Stem Cells, vol. 35, 2017 (published on web Aug. 20, 2017), pp. 2280-2291.
Extended European Search Report for corresponding European Application No. 15827606.3, dated Feb. 21, 2018.

(Continued)

Primary Examiner — Arthur S Leonard
(74) Attorney, Agent, or Firm — Birch, Stewart, Kolasch & Birch, LLP (57) ABSTRACT The present invention aims to obtain a method for quality evaluation of human mesenchymal stem cells, a method for isolation, selection and culture of human mesenchymal stem cells, a cell population of rapidly proliferating human mesenchymal stem cells, as well as monoclonal antibodies that specifically recognize rapidly proliferating human mesenchymal stem cells.
From a cell population containing human mesenchymal stem cells, rapidly proliferating human mesenchymal stem cells are isolated, selected and cultured. The abundance ratio of cells expressing Ror2 or Fzd5 in the cell population thus isolated, selected and cultured is quantified to determine whether or not each cell population is acceptable.

7 Claims, 8 Drawing Sheets (56) References Cited

OTHER PUBLICATIONS

Holley et al., "Comparative Quantification of the Surfaceome of Human Multipotent Mesenchymal Progenitor Cells," Stem Cell Reports (Mar. 10, 2015), vol. 4, pp. 473-488.
International Search Report dated Sep. 29, 2015, in PCT International Application No. PCT/JP2015/071770.
Japanese Office Action, dated Mar. 3, 2020, for Japanese Application No. 2016-538462, along with an English translation.
Kolben et al., "Dissecting the impact of Frizzled receptors in Wnt/β-catenin signaling of human mesenchymal stem cells," Biol. Chem. (2012), vol. 393, No. 12, pp. 1433-1447.
Kotobuki et al., Cultured Autologous Human Cells for Hard Tissue Regeneration: Preparation and Characterization of Mesenchymal Stem Cells from Bone Marrow, Artificial Organs., 2004; 28(1):33-39 (Year: 2004).
Liu et al., "The Orphan Receptor Tyrosine Kinase Ror2 Promotes Osteoblast Differentiation and Enhances ex Vivo Bone Formation," Molecular Endocrinology, vol. 21, No. 2, 2007 (published on web Nov. 9, 2006), pp. 376-387.
Mabuchi et al., "LNGFR$^+$THY-1$^+$VCAM-1$^{hi+}$Cells Reveal Functionally Distinct Subpopulations in Mesenchymal Stem Cells," Stem Cell Reports (Aug. 6, 2013), vol. 1, pp. 152-165.
Miyamoto et al., "Elucidation of undifferentiated state-maintaining mechanism by human mesenchymal stem cell-specific miRNA," Japan Regenerative Medicine Association Magazine, Extra issue (2014), vol. 13, Suppl, p. 317, (with English translation).
Pittenger et al., "Multilineage potential of adult human mesenchymal stem cells," Science (1999), vol. 284, pp. 143-147.
Rider et al., Selection using the alpha-1 integrin (CD49a) enhances the multipotentiality of the mesenchymal stem cell population from heterogeneous bone marrow stromal cells, J Mol Hist (2007) 38:449-458 (Year 2007).
Shen et al., "Bone marrow mesenchymal stem celt-derived Wnt5a inhibits leukemia cell progression in vitro via activation of the non-canonical Wnt signaling pathway," Oncology Letters (May 7, 2014), vol. 8. pp. 85-90.
Singapore Written Opinion, dated Sep. 25, 2019, for Singapore Application No. 11201610795V.
Suresh el al., Advantages of bispecific hybridomas in one-step immunocytochemistry and immunoassays. Proc Natl Acad Sci U.S.A., Oct. 1986; 83(20): 7989-7993 (Year 1986).
Toma et al., Human Mesenchymal Stem Cells Differentiate to a Cardiomyocyte Phenotype in the Adult Murine Heart, Circulation, 2002, 105:93-98 (Year: 2002).
Tormin et al., "Prospective identification and Characterization of Human Mesenchymal Stem Cell Subpopulations," Blood (2006), vol. 1008, No. 2559 (Abstract).
Wacker et al., Analysis of One-Step and Two-Step Real-Time RT-PCR Using Superscript III (J Bio Tech, 2005, 16:266-271)(Year:2005).
Xin et al., "The Wnt5a/Ror2 pathway is associated with determination of the differentiation fate of bone marrow mesenchymal stem cells in vascular calcification," International Journal of Molecular Medicine (2013), vol. 31, pp. 583-588.
English translation of Japanese Notice of Reasons for Refusal for Japanese Application No. 2021-040712, dated Apr. 12, 2022.
Examiner's Report for Canadian Application No. 2,954,245, dated Apr. 21, 2022.

\* cited by examiner

METHOD FOR EVALUATING QUALITY OF HUMAN MESENCHYMAL STEM CELL, AND MONOCLONAL ANTIBODY FOR USE IN SAID METHOD

This application is a Continuation of copending application Ser. No. 15/321,679 filed on Dec. 22, 2016, which is the U.S. National Phase of PCT/JP2015/071770, filed Jul. 31, 2015, and which claims priority under 35 U.S.C. § 119(a) to Application No. 2014-157367 filed in Japan on Aug. 1, 2014, the entire contents of all of which are expressly incorporated by reference into the present application.

TECHNICAL FIELD

The present invention relates to a method for quality evaluation of human mesenchymal stem cells, a method for isolation, selection and culture of human mesenchymal stem cells, a cell population of rapidly proliferating human mesenchymal stem cells, as well as monoclonal antibodies that specifically recognize rapidly proliferating human mesenchymal stem cells.

BACKGROUND ART

Mesenchymal stem cells (MSCs) are a kind of somatic stem cells which are increasingly used for clinical applications, after hematopoietic stem cells, because they have fewer ethical problems associated with cell collection and have differentiation potency into various types of tissues such as bone, cartilage, fat, etc. Mesenchymal stem cells can be isolated through relatively simple manipulations as described later, and therefore are widely used as materials for biomaterials, for example, by being induced to differentiate into cartilage, bone and others mainly in test tubes and then used for local transplantation.

As a method for isolation and culture of human mesenchymal stem cells, the culture method reported in Non-patent Document 1 is commonly used. However, a cell population obtained by such a conventional method contains many contaminant cells of less quality (which have lost their differentiation, proliferation and migration potency), and these contaminant cells serve as a factor causing further loss of quality because they affect the cells which should have inherently had potential.

Under these conventional circumstances, there has been established a method for isolation and culture of human mesenchymal stem cells, which achieves higher proliferation potency, differentiation potency and migration potency than those in conventional methods (Non-patent Documents 2 and 3 and Patent Document 1). According to these Non-patent Documents 2 and 3 and Patent Document 1, antibodies against CD271 (LNGFR) and CD90 (Thy1) are used to select LNGFR$^+$ Thy1$^+$ cells from human bone marrow, placental chorion, fat tissue, peripheral blood, dental pulp and so on, whereby human mesenchymal stem cells can be enriched.

Moreover, the selected LNGFR$^+$ Thy1$^+$ cells are subjected to single cell (clone) culture to select a rapidly expanding lot (REC: Rapidly Expanding Clone), whereby human mesenchymal stem cells excellent in proliferation potency, differentiation potency and migration potency can be obtained in high purity.

The high purity human mesenchymal stem cells (RECs) thus obtained were found to have proliferation potency, differentiation potency and migration potency which were all 1000-fold or more higher than those of mesenchymal stem cells obtained by conventional methods.

According to the features of the above method for isolation and culture of human mesenchymal stem cells, single cell culture allows the formation of conditions free from contaminant cells and thus enables expansion culture while maintaining cell quality. In particular, because of retaining migration potency, the resulting cells can be administered via the intravenous route, and therefore can be expected for use in serious systemic diseases such as bone and cartilage hypoplasia.

PRIOR ART DOCUMENTS

Patent Documents

Patent Document 1: JP 2009-60840 A

Non-Patent Documents

Non-patent Document 1: Pittenger, M. F., Mackay, A. M., Beck, S. C., Jaiswal, R. K., Douglas, R., Mosca, J. D., Moorman, M. A., Simonetti, D. W., Craig, S., and Marshak, D. R. (1999). Multilineage potential of adult human mesenchymal stem cells. Science 284, 143-147.

Non-patent Document 2: Mabuchi Y, Morikawa S, Harada S, Niibe K, Suzuki S, Renault-Mihara F, Houlihan D D, Akazawa C, Okano H, Matsuzaki Y. (2013). LNGFR+ THY-1+VCAM-1hi+ Cells Reveal Functionally Distinct Subpopulations in Mesenchymal Stem Cells. Stem Cell Reports 1, 152-165.

Non-patent Document 3: CGH array data, Gene Expression Omnibus (GEO) (accession number: GSE34484)

SUMMARY OF THE INVENTION

Problem to be Solved by the Invention

Unlike immortalized cell lines, even RECs cannot avoid the loss of cell quality when repeatedly subcultured over a long period of time. However, at present, there is no accurate indicator for the loss of quality.

The present invention aims to provide a method for quality evaluation of human mesenchymal stem cells, a method for isolation, selection and culture of human mesenchymal stem cells, a cell population of rapidly proliferating human mesenchymal stem cells, as well as monoclonal antibodies that specifically recognize rapidly proliferating human mesenchymal stem cells.

In addition, gene expression analysis was performed between RECs and the other clones of less quality (MEC: Moderately Expanding Clone, SEC: Slowly Expanding Clone) to thereby select REC-specific genes. The present invention further aims to prepare novel monoclonal antibodies that recognize proteins expressed from the specific genes.

Means to Solve the Problem

To achieve the above aim, the method for quality evaluation of human mesenchymal stem cells according to the present invention is characterized in that from a cell population containing human mesenchymal stem cells, rapidly proliferating human mesenchymal stem cells are isolated, selected and cultured, and cells expressing Ror2 or Fzd5 (or the abundance ratio thereof) in the cell population thus isolated, selected and cultured are quantified to determine whether or not each cell population is acceptable. According to this constitution, Ror2 or Fzd5 when expressed alone allows determination of whether or not a cell population is composed of RECs, and the determination can be made in a simpler manner because cultured cells may also be used for this purpose. It should be noted that LNGFR is not expressed in cultured cells even when they are RECs, and Thy1 when expressed alone does not allow determination of whether or not a cell population is composed of RECs.

In the above constitution, cells expressing Ror2 or Fzd5 may be quantified by using anti-Ror2 monoclonal antibody or anti-Fzd5 monoclonal antibody. In this case, mRNA expression of Ror2 may be quantified by quantitative PCR, or alternatively, cells expressing Ror2 or Fzd5 may be quantified by immunostaining. However, it should be noted that Ror2 is expressed extracellularly and hence analyzed by flow cytometry (hereinafter referred to as "FCM") is easily applicable for the above purpose, whereas Fzd5 is expressed intracellularly and visual evaluation such as immunostaining is therefore suitable for the above purpose.

On the other hand, to achieve the above aim, the method for isolation, selection and culture of human mesenchymal stem cells is characterized in that from a cell population containing human mesenchymal stem cells, rapidly proliferating human mesenchymal stem cells are isolated, selected and cultured, and cells expressing Ror2 or Fzd5 (or the abundance ratio thereof) in the cell population thus isolated, selected and cultured are quantified to determine whether or not each cell population is acceptable, thus selecting only the cell population(s) determined to be acceptable.

In this constitution, cells expressing Ror2 or Fzd5 may be quantified by using anti-Ror2 monoclonal antibody or anti-Fzd5 monoclonal antibody. In this case, cells expressing mRNA of Ror2 may be quantified by quantitative PCR, or alternatively, cells expressing Ror2 or Fzd5 may be quantified by immunostaining.

Moreover, the above step where rapidly proliferating human mesenchymal stem cells are isolated, selected and cultured may comprise a step where the cell population containing human mesenchymal stem cells is analyzed by FCM for cells stained simultaneously with anti-LNGFR monoclonal antibody and anti-Thy1 monoclonal antibody to thereby effect cell sorting of LNGFR$^+$ Thy1$^+$ cells. Without being limited to this embodiment, the above step where rapidly proliferating human mesenchymal stem cells are isolated, selected and cultured may alternatively comprise a step where the cell population containing human mesenchymal stem cells is analyzed by FCM for cells stained with anti-Ror2 monoclonal antibody to thereby effect cell sorting of Ror2$^+$ cells.

Further, the above methods may each comprise a step where the above cell population is directly prepared from cells derived from each tissue, including bone marrow. On the other hand, the method comprising the step of effecting cell sorting of Ror2$^+$ cells may comprise a step where the above cell population is prepared by adherent culture of cells derived from each tissue, including bone marrow. This is because cultured cells of RECs are not positive for LNGFR but are positive for Ror2.

In the above methods, the above cell sorting step may comprise a step where the positive cells are seeded in wells of a culture plate and the cells in each well reaching confluence upon culture are then isolated and selected.

To achieve the above aim, the cell population of rapidly proliferating human mesenchymal stem cells is characterized in that from a cell population containing human mesenchymal stem cells, rapidly proliferating human mesenchymal stem cells are isolated, selected and cultured, and cells expressing Ror2 or Fzd5 (or the abundance ratio thereof) in the cell population thus isolated, selected and cultured are quantified to determine whether or not each cell population is acceptable, thus selecting only the cell population(s) determined to be acceptable.

In this characteristic, the cell population containing human mesenchymal stem cells may be analyzed by FCM for cells stained simultaneously with anti-LNGFR monoclonal antibody and anti-Thy1 monoclonal antibody to thereby effect cell sorting of LNGFR$^+$ Thy1$^+$ cells, and these dual positive cells may be seeded in wells of a culture plate and the cells in each well reaching confluence upon culture may be isolated and selected, prior to the above quantification.

Alternatively, in this characteristic, the cell population containing human mesenchymal stem cells may be analyzed by FCM for cells stained with anti-Ror2 monoclonal antibody to thereby effect cell sorting of Ror2$^+$ cells, and these positive cells may be seeded in wells of a culture plate and the cells in each well reaching confluence upon culture may be isolated and selected, prior to the above quantification.

To achieve the above aim of the present invention, a novel monoclonal antibody according to the present invention is anti-Ror2 monoclonal antibody whose clone name is 7C9. In addition, another novel monoclonal antibody according to the present invention is anti-Fzd5 monoclonal antibody whose clone name is 6F5.

Effects of the Invention

Proteins encoded by the identified two genes (Fzd5 and Ror2: their details will be described later) are expressed specifically in RECs, and their expression is not observed in cell populations of less quality. Moreover, these genes are essential for maintaining the undifferentiated state of RECs, and they serve as effective indicators which are closely related to cell functions and ensure cell performance, but not serve as mere biomarkers, in light of the following results: 1) inhibition of their expression incudes loss of cell performance; and 2) forced expression of these genes allows prolonged undifferentiated state, etc.

As described above, the present invention enables the provision of a method for quality evaluation of human mesenchymal stem cells, a method for isolation, selection and culture of human mesenchymal stem cells, a cell population of rapidly proliferating human mesenchymal stem cells, as well as monoclonal antibodies that specifically recognize rapidly proliferating human mesenchymal stem cells.

Other aims, constitutions and effects of the present invention will become apparent from the embodiments of the invention shown below.

isolated and cultured in Step 1, and the cultured RECs are evaluated in Step 2. Some exemplary combinations of these steps are listed in Table 1. All combinations except for those expressed as "Unable" in the column "Process evaluation" are able to be implemented. First, the combinations under Process Nos. P1 and P2 will be described below.

TABLE 1

| Process No. | Cell source | FCM | Step 1 | | | Step 2 | | Comment |
| | | | Sorting | Culture | Well treatment | Cell evaluation | Process evaluation | |
|---|---|---|---|---|---|---|---|---|
| P1 | Tissue (e.g., bone marrow) | LNGFR$^+$ Thy1$^+$ | Single | Culture for 2 weeks | Selection of confluent wells | Ror2$^+$ | Very good | Evaluation is possible while ensuring cell performance |
| P2 | Tissue (e.g., bone marrow) | LNGFR$^+$ Thy1$^+$ | Single | Culture for 2 weeks | Selection of confluent wells | Fzd5$^+$ | Good | Fzd5 is expressed intracellularly and hence difficult to determine by FCM, but can be evaluated by immunostaining or the like while ensuring cell functions |
| P3 | Tissue (e.g., bone marrow) | LNGFR$^+$ Thy1$^+$ | Single | Culture for 2 weeks | Selection of confluent wells | Thy1$^+$ | Unable | THY1 is also expressed in MECs and SECs and hence cannot be used for evaluation |
| P4 | Tissue (e.g., bone marrow) | LNGFR$^+$ Thy1$^+$ | Single | Culture for 2 weeks | Selection of confluent wells | LNGFR$^+$ | Unable | LNGFR is not expressed in cultured cells |
| P5 | Tissue (e.g., bone marrow) | LNGFR$^+$ Thy1$^+$ | Multiple | Culture for 2 weeks | Selection of confluent wells | Ror2$^+$ | Less good | The proportion of cells other than RECs can be quantified, but purity is low |
| P6 | Tissue (e.g., bone marrow) | Ror2$^+$ | Single | Culture for 2 weeks | Selection of confluent wells | Ror2$^+$ | Good | Sorting using Ror2 as an indicator results in a lower enrichment rate when compared to the LNGFR$^+$ Thy1$^+$ case |
| P7 | Tissue (e.g., bone marrow) | Ror2$^+$ | Single | Culture for 2 weeks | Selection of confluent wells | Fzd5$^+$ | Good | Fzd5 is expressed intracellularly and hence difficult to determine by FCM, but can be evaluated by immunostaining or the like while ensuring cell functions |
| P8 | Tissue (e.g., bone marrow) | Fzd5$^+$ | Single | Culture for 2 weeks | Selection of confluent wells | Ror2$^+$ | Unable | Fzd5 is expressed intracellularly and hence difficult to detect by FCM, and is therefore difficult to use as a marker for cell isolation |
| P9 | Tissue (e.g., bone marrow) | Ror2+$^+$ | Multiple | Culture for 2 weeks | Selection of confluent wells | Ror2$^+$ | Less good | The proportion of cells other than RECs can be quantified, but purity is low |
| P10 | Adherent cultured cells | LNGFR$^+$ Thy1$^+$ | Single | Culture for 2 weeks | Selection of confluent wells | Ror2$^+$ | Unable | LNGFR is not expressed in cultured cells, while THY1 is also expressed in cells other than RECs |
| P11 | Adherent cultured cells | Ror2$^+$ | Single | Culture for 2 weeks | Selection of confluent wells | Ror2$^+$ | Good | Evaluation is possible while ensuring cell performance |
| P12 | Adherent cultured cells | Ror2$^+$ | Single | Culture for 2 weeks | Selection of confluent wells | Fzd5$^+$ | Good | Fzd5 is expressed intracellularly and hence difficult to determine by FCM, but can be evaluated by immunostaining or the like while ensuring cell functions |
| P13 | Adherent cultured cells | Fzd5$^+$ | Single | Culture for 2 weeks | Selection of confluent wells | Ror2$^+$ | Unable | Fzd5 is expressed intracellularly and hence difficult to detect by FCM, and is therefore difficult to use as a marker for cell isolation |
| P14 | Adherent cultured cells | Ror2$^+$ | Multiple | Culture for 2 weeks | Selection of confluent wells | Ror2$^+$ | Less good | The proportion of cells other than RECs can be quantified, but purity is low |
| P15 | Adherent cultured cells | Ror2$^+$ | Single | — | — | — | Good | Used without cell evaluation |

DESCRIPTION OF EMBODIMENTS

Figure 1:
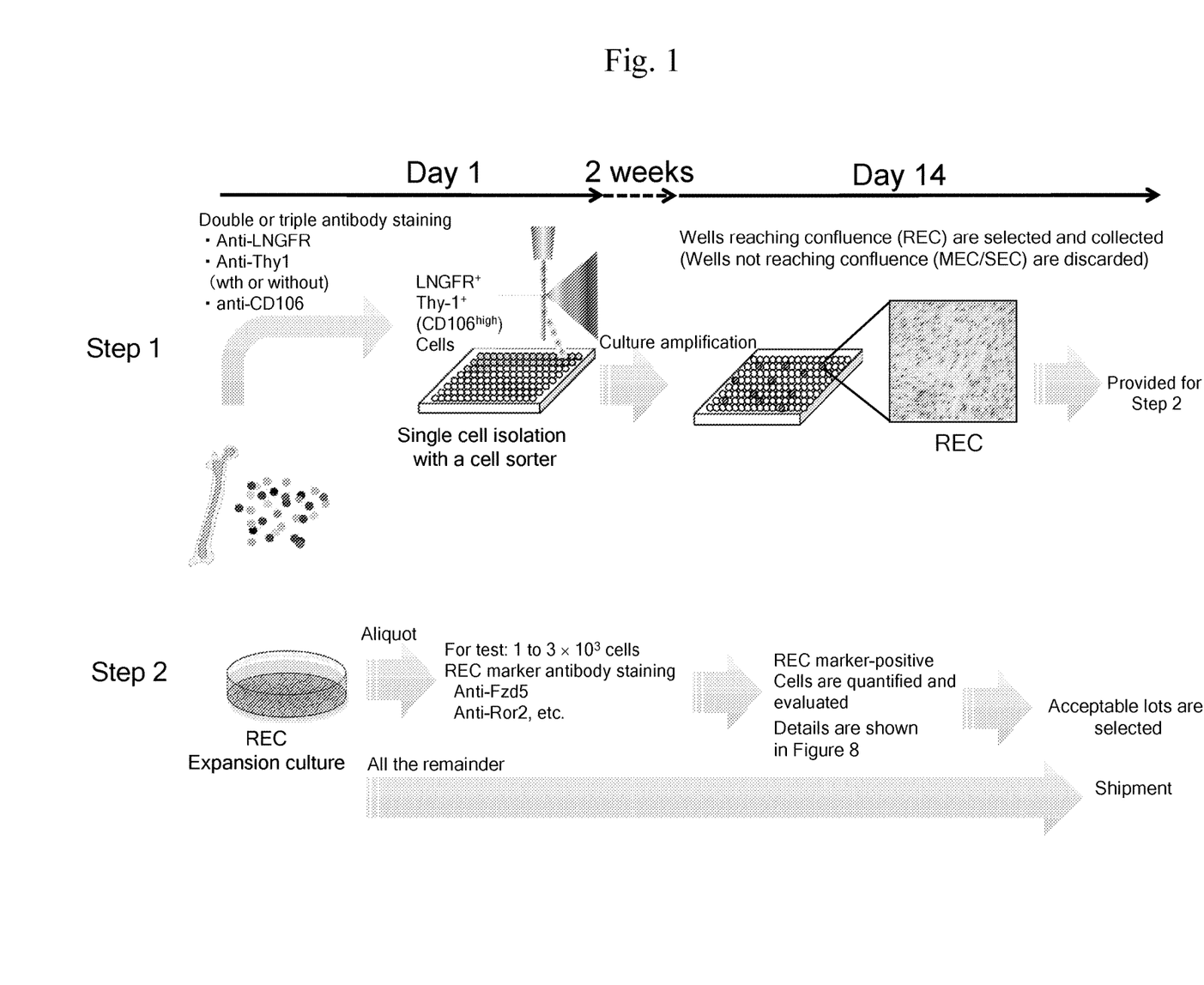
FIG. 1 shows the steps of selection, isolation, culture and quality evaluation of high quality mesenchymal stem cells (RECs).

While referring to the drawings, the steps of selection, isolation and culture of RECs will be outlined below, followed by explanations about the purpose and details of each step. In the present invention, RECs are selected,

[Step 1] FIG. 1 illustrates the step of REC isolation by the single clone culture method.

1) Mononuclear cells are prepared from human bone marrow (or fat or placental chorion) and these bone marrow mononuclear cells are stained with anti-LNGFR and anti-Thy1 (LNGFR$^+$ Thy1$^+$ cells are referred to as LT cells).

2) Flow cytometry (FCM, cell sorter) is used to effect clone sorting of LNGFR$^+$ Thy1$^+$ cells in a 96-well culture plate (i.e., one cell is seeded per well; expressed as "Single" in Table 1).

It should be noted that anti-CD106 monoclonal antibody may be added to effect clone sorting of LNGFR$^+$Thy1$^+$ cells that are also strongly positive for CD106.

3) After single cell culture for 2 weeks, the culture plate was observed under a microscope to select wells reaching confluence, and the cells contained in each of these wells are determined to be RECs (Rapidly Expanding Cells). Wells showing delayed cell expansion, i.e., MECs/SECs (Moderately/Slowly Expanding Cells) are discarded.

4) The cells contained in the wells selected as RECs are collected separately on a well-by-well basis. RECs collected from one well are defined as one lot.

[Step 2] FIG. 1 further shows the evaluation of cultured cells using REC markers (anti-Ror2 and anti-Fzd5).

1) The RECs collected from the 96-well plate are transferred to culture dishes or culture flasks on a well-by-well basis, and cultured to reach confluence (expansion culture).

2) After expansion culture, the cells grown in adherent state are collected from all lots, and an aliquot (about 1 to 3×10$^3$ cells) of each lot is sampled and single-stained with a monoclonal antibody against each REC marker (anti-Ror2 or anti-Fzd5).

3) REC marker-positive cells are analyzed by flow cytometry to determine the ratio of the REC marker-positive cells in the collected cells (mRNA expression of Ror2 may be quantified by quantitative PCR, or alternatively, this ratio may be determined manually under a microscope).

4) If the above positive ratio is equal to or greater than a given value (e.g., 65%), such a lot (cell population) is determined to be acceptable.

5) Cells in the acceptable lots are filled into freezing vials and stored in liquid nitrogen.

6) These frozen cells are defined as high quality human mesenchymal stem cells (product).

7) After the cells in each vial are thawed and then expanded on a culture dish or flask, a user is finally able to use at least 1×10$^{10}$ high purity mesenchymal stem cells in a stable manner.

In the above steps, clone sorting of LT cells may be replaced with clone sorting of Ror2$^+$ cells (P6 and P7 in Table 1). Moreover, LT cells or Ror2$^+$ cells may be selected and seeded in groups of two or more per well of a 96-well culture plate (expressed as "Multiple" in Table 1; P5, P9 and P14). In this case, however, the purity is lower than that in clone sorting. It should be noted that the term "confluence" or "confluent" refers to a state where 90% or more of the culture vessel surface is coated with cultured cells. Likewise, the term "semi-confluence" or "semi-confluent" refers to a state where 70% to 80% of the culture vessel surface is coated with cultured cells. The size and type of culture devices to be used may be changed as appropriate depending on the growth rate of cells.

In the above embodiment, the above cell population is directly prepared from cells derived from each tissue, including bone marrow. However, in the case of sorting for Ror2$^+$ cells, the above cell population may be prepared by adherent culture of cells derived from each tissue, including bone marrow (P10 to P15 in Table 1; expressed as "Adherent cultured cells"). In this case, bone marrow mononuclear cells are seeded on a medium supplemented with 10% to 20% serum and bFGF (at 37° C. under 1% to 5% $CO_2$) and cultured for about 2 weeks to collect fibroblast-like adherent cells (CFU-F) appearing after culture. The step of preparing a cell population may comprise treatment of bone marrow with collagenase. Alternatively, this step may be designed such that a cell population is prepared from peripheral blood after G-CSF administration.

It should be noted that the evaluation prior to shipment (Step 2-2) and Step 2-3)) is not always necessary, and adherent cultured cells may be used and subjected to FCM sorting to isolate Ror2$^+$ cells, optionally followed by expansion culture, and the thus obtained cells may be provided for treatment in Step 2-5) and the subsequent steps prior to shipment, as in Process P15 in Table 1.

Figure 2:
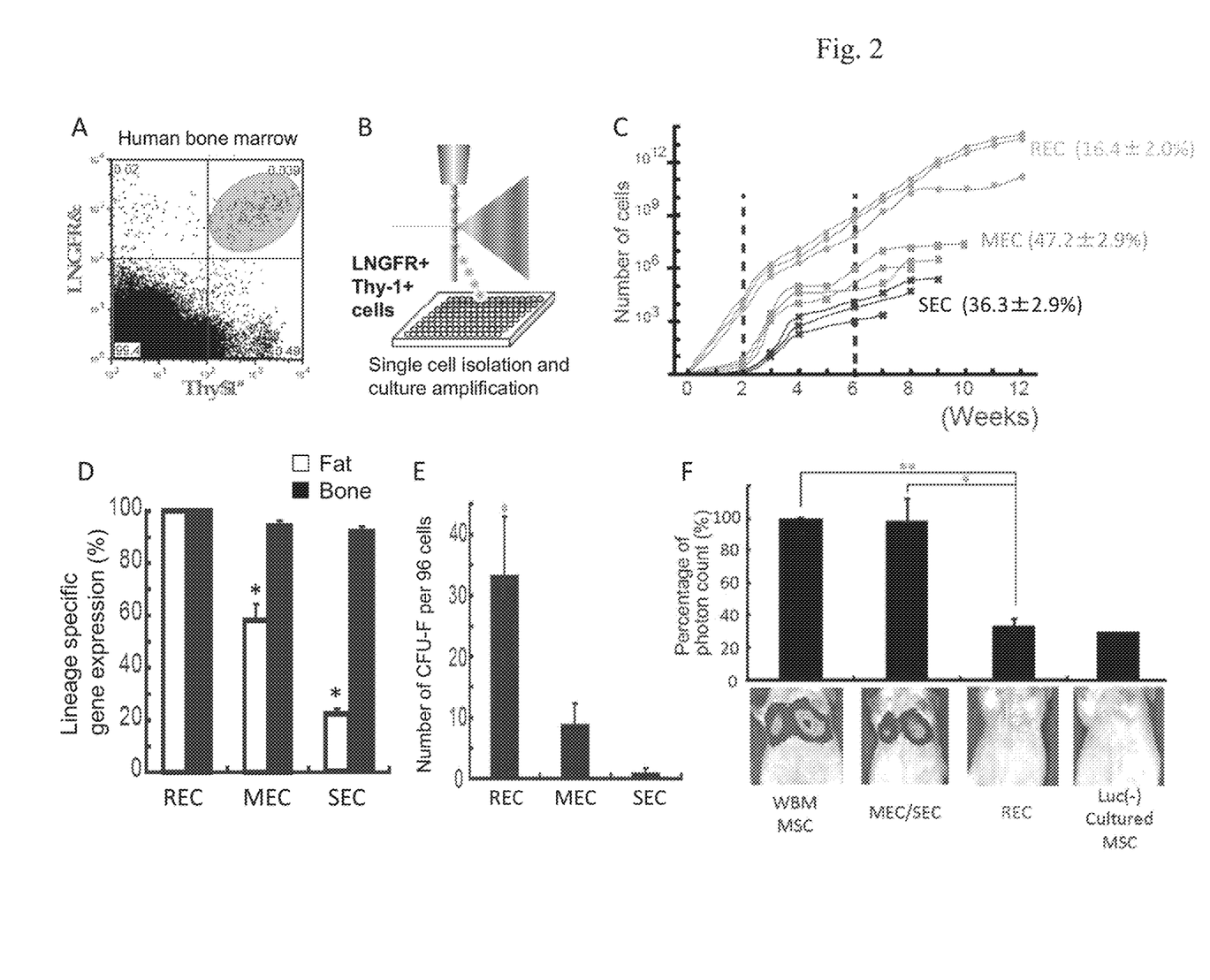
FIG. 2 shows the results compared for various parameters among RECs, MECs and SECS.

While referring to FIG. 2, a comparison will now be made of cell performance between RECs and MECs/SECs. FIG. 2 shows the results obtained when RECs, MECs and SECs were compared for their cell performance using various parameter data.

FIG. 2A shows the results obtained when human bone marrow mononuclear cells were stained with antibodies against LNGFR and Thy1, followed by FCM analysis. The area within the ellipse represents LT cells.

FIG. 2B is a schematic diagram for single cell isolation (clone sorting) of LT cells in a 96-well plate.

FIG. 2C is a graph showing the results measured for cell counts after single cell culture at fixed time intervals. RECs show a higher proliferation rate than MECs/SECs, and their count reaches 0.5 to 1×10$^4$ within about 2 weeks. A cell count of 0.5 to 1×10$^4$ is required to establish confluence in a well of a 96-well plate.

FIG. 2D shows the results obtained when RECs, MECs and SECs were induced to differentiate into bone and fat, followed by quantitative PCR to analyze gene expression specific to bone and fat cells. RECs were found to be particularly high in differentiation potency into fat cells when compared to MECs and SECs.

FIG. 2E is a graph showing the results obtained when RECs, MECs and SECs were seeded again in a 96-well plate by clone sorting and wells showing secondary colony formation were then counted and compared. Secondary colony formation serves as an indicator for self-replication potency which is indicative of the undifferentiated state. About 33% of RECs show secondary colony formation, whereas only a few colonies are formed from MECs/SECs.

FIG. 2F shows the results obtained when the following cell populations, each having been transformed with a Luc (luciferase) gene expression vector, i.e., WBMs (MSCs obtained in a standard manner; WBM is an abbreviation for Whole Bone Marrow), RECs and MECs/SECs, as well as non-luciferase-labeled WBMs prepared as a negative control group (Luc(−) Cultured MSCs) were each administered to immunodeficient mice via the intravenous route, followed by intraperitoneal administration of luciferin serving as a substrate for Luc to observe luminescence from luciferase by using an in vitro detection system (IVIS) at 24 hours after transplantation. The upper panel shows a graph obtained as follows: Luc luminescence intensity in each mouse was expressed numerically and, relative to the WBM MSC-transplanted group which was set to 100%, the luminescence ratio (%) was plotted for the mice transplanted with the other cells. The lower panel shows images of Luc luminescence in the recipient mice of the respective groups. As can be seen from these results, the REC-transplanted mice show extremely low luminescence intensity in their lungs, thus indicating that RECs are rarely trapped into capillary vessels in the lungs, whereas MECs/SECs are trapped almost at the same level as WBMs (cultured MSCs obtained in a standard manner) and remain in the lungs.

In view of all the above results, RECs are a cell population excellent in proliferation potency, differentiation potency and migration potency, and are particularly advantageous in that they have migration potency comparable to that of MSCs in fresh bone marrow, in terms of being able to be administered systemically against intractable diseases as described later.

According to the experiments made by the inventors, including those shown above, RECs are characterized by the following, when compared to normal MSCs:

1. being a morphologically very uniform cell population;
2. showing no cellular aging;
3. having a high division rate and being able to be cultured and amplified while retaining the undifferentiated nature;
4. begin a cell population easy to differentiate into bone and fat due to high differentiation potency; and
5. retaining migration potency RECs are the most undifferentiated cell population among human MSCs, and have the most similar properties to MSCs in bone marrow. Moreover, when compared to MECs/SECs or MSCs obtained in a standard manner, RECs are a fresh and less mutated cell population ensuring cell performance due to their higher differentiation, proliferation and migration potency.

Figure 3:
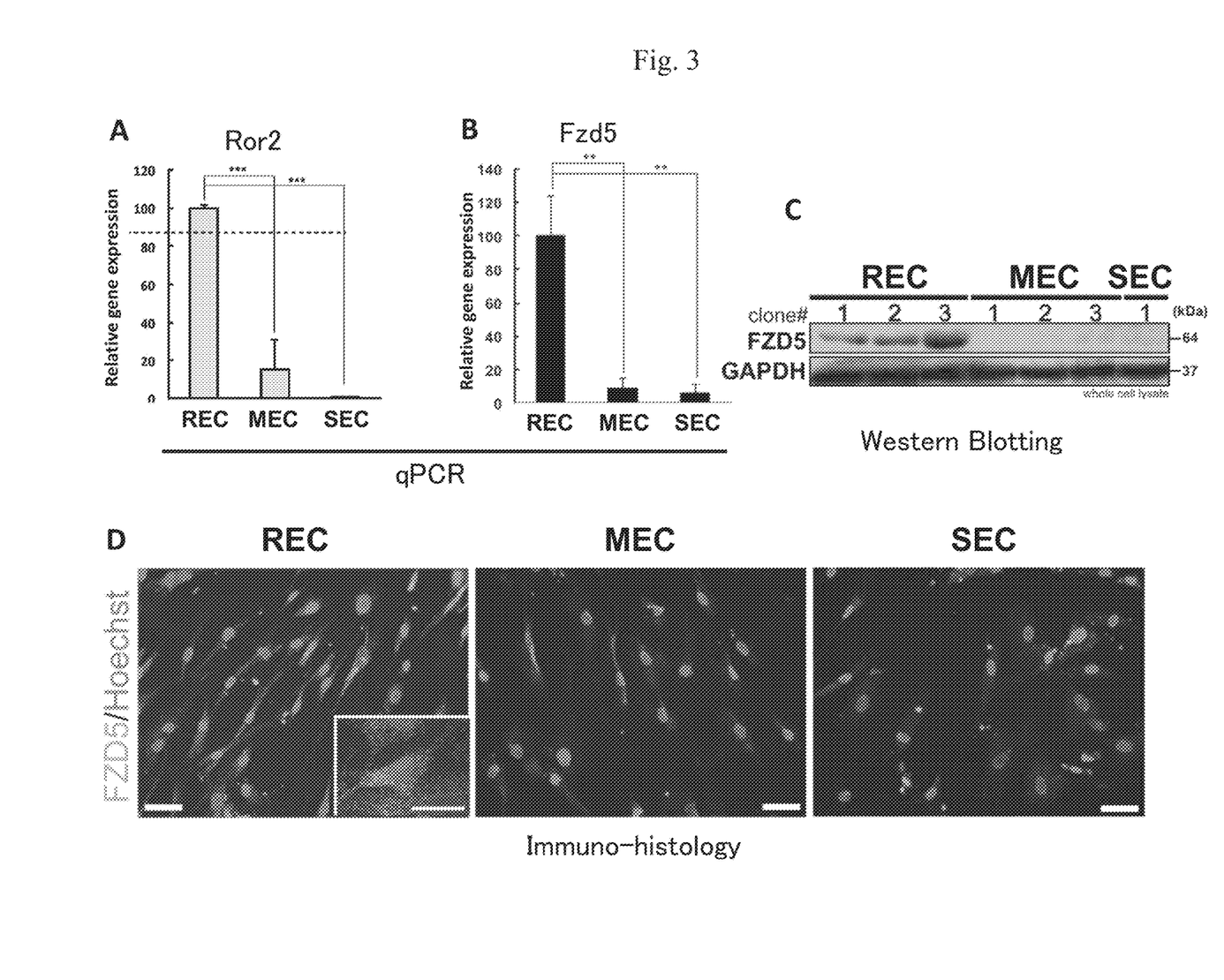
FIG. 3 shows figures and graphs which indicate that Ror2 and Fzd5 are expressed specifically in RECs.

Next, while referring to FIG. 3, an explanation will be made about the identification of undifferentiated MSC (REC)-specific genes Ror2 and Fzd5.

The expression levels of genes expressed in RECs, MECs and SECs were compared by the DNA array method, thus confirming that Fzd5, which is one of the Wnt receptors, and its co-receptor Ror2 were both specific to RECs.

FIG. 3A shows a comparison of Ror2 mRNA expression in RECs, MECs and SECs, as measured by quantitative PCR.

FIG. 3B shows a comparison of Fzd5 mRNA expression in RECs, MECs and SECs, as measured by quantitative PCR.

FIG. 3C shows a comparison of Fzd5 protein expression, as measured by Western blotting.

FIG. 3D shows photographs compared for intracellular localization of Fzd5 protein, as observed by immunofluorescent staining.

As a result of evaluation by the above several analysis methods, it can be confirmed that the expression of Fzd5 and Ror2 is specific to RECs. Thus, the respective expression of Fzd5 and Ror2, when detected and quantified, would be effective as an indicator for cell quality evaluation of RECs. Moreover, the newly prepared anti-Fzd5 monoclonal antibody and anti-Ror2 monoclonal antibody are able to detect and quantify their target protein antigens in any technique selected from flow cytometry, Western blotting and immunofluorescent staining.

Figure 4:
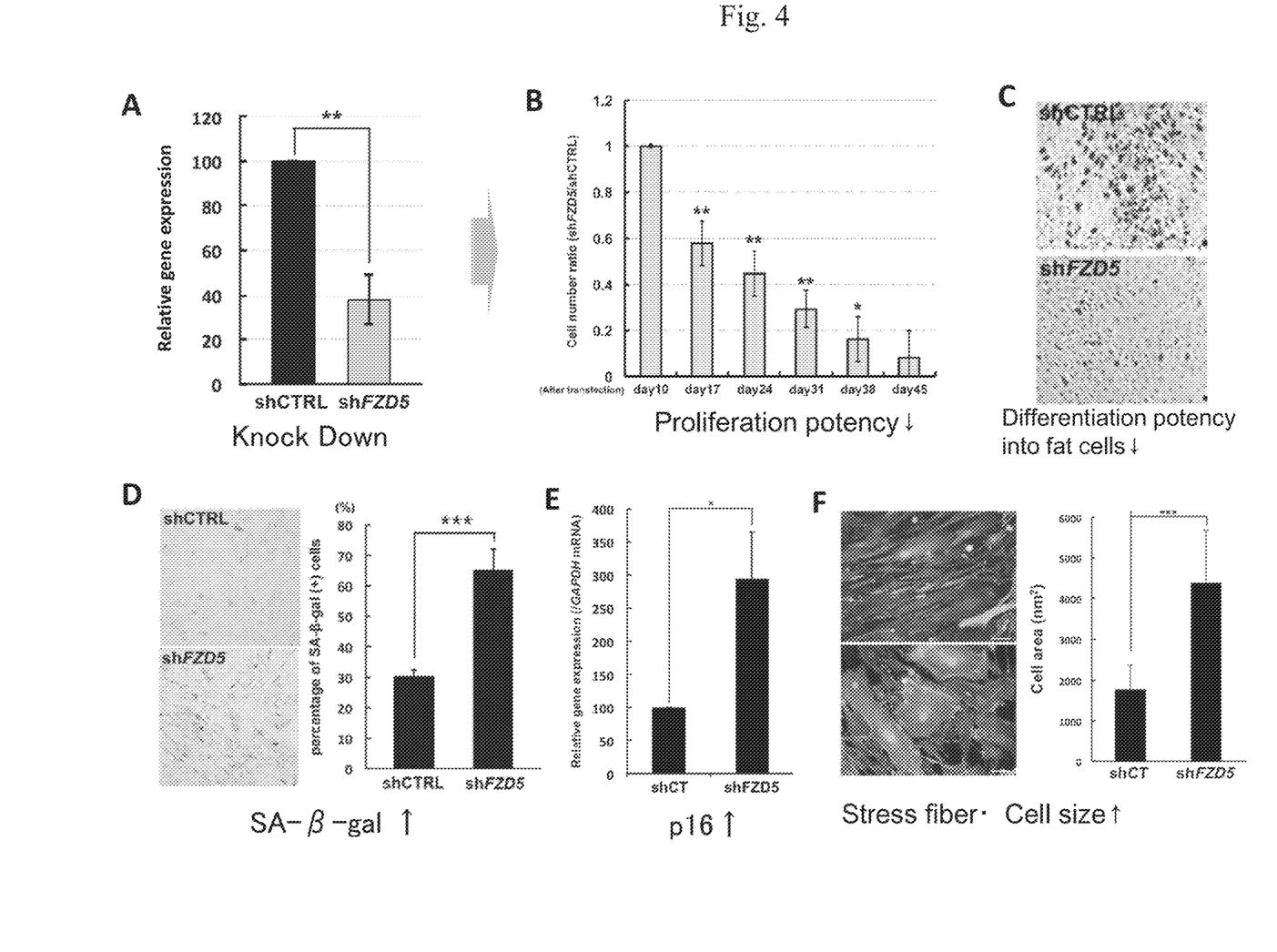
FIG. 4 shows figures and graphs which indicate that inhibition of Fzd5 induces loss of cell properties in RECs.

Next, while referring to FIG. 4, an examination will be made of cellular aging induction by loss of function of Fzd5.

The RNA interference method is a technique to examine the function of a target gene by introduction of short RNA (shRNA) having a sequence complementary to target mRNA into cells to thereby disrupt the target mRNA. FIG. 4 shows the results obtained from a series of experiments on cell properties in RECs when Fzd5 mRNA was disrupted by shRNA having a sequence complementary to Fzd5 (shFZD5), in comparison with the control group (shCTRL; shRNA having a random sequence not complementary to Fzd5).

FIG. 4A is a graph showing the mRNA level of Fzd5, as quantified by quantitative PCR, after introduction of shFZD5 or shCTRL into RECs. When the mRNA level of Fzd5 in the control group (shCTRL, short hairpin control) was set to 100, the mRNA level of Fzd5 was reduced to about 40% in RECs forced to express shFZD5.

FIG. 4B is a graph whose vertical axis plots cell counts in the group forced to express shFZD5 after introduction of shFZD5 or shCTRL into RECs, relative to cell counts in the control group which are set to 1, and whose horizontal axis plots the number of days after shRNA introduction. RECs forced to express shFZD5 showed a sudden reduction in their cell count when compared to the control group, thus suggesting that Rzd5 inhibition would induce a reduction in proliferation potency.

FIG. 4C shows images of fat droplets stained with Oil-Red-O at 14 days of culture, after introduction of shFZD5 or shCTRL into RECs and the subsequent induction of their differentiation into fat cells. Fzd5 inhibition was found to induce a reduction in differentiation potency into fat cells, when compared to the control group.

The activity of SA-$\beta$-gal serving as an indicator for cellular aging can be detected by blue staining upon addition of its substrate X-gal. FIG. 4D shows images stained by x-gal staining after introduction of shFZD5 or shCTRL into RECs, along with a graph which plots the frequency of cells having SA-$\beta$-gal activity in each cell population.

FIG. 4E is a graph showing the mRNA level of p16 (INK4a) serving as an indicator for cellular aging, as quantified by quantitative PCR. When the control group was set to 100, the mRNA level of p16 in shFZD5-receiving RECs was about 300, thus indicating that inhibition of Fzd5 expression induced cellular aging.

FIG. 4F shows images observed for stress fiber formation by intracellular staining with anti-F-actin antibody in each cell population after introduction of shFZD5 or shCTRL into RECs, along with a graph which plots the averaged area (cell size) of individual cells in these respective cell populations.

In view of the above results, inhibition of the Fzd5 function in RECs induces a reduction in proliferation potency, a reduction in differentiation potency, cellular aging, as well as a reduction in migration potency and an increase in cell size due to stress fiber formation, thus resulting in the same properties as in MECs/SECs. This suggests that Fzd5 would be a functional molecule ensuring the maintenance of cell performance in RECs, but is not a mere biomarker.

Figure 5:
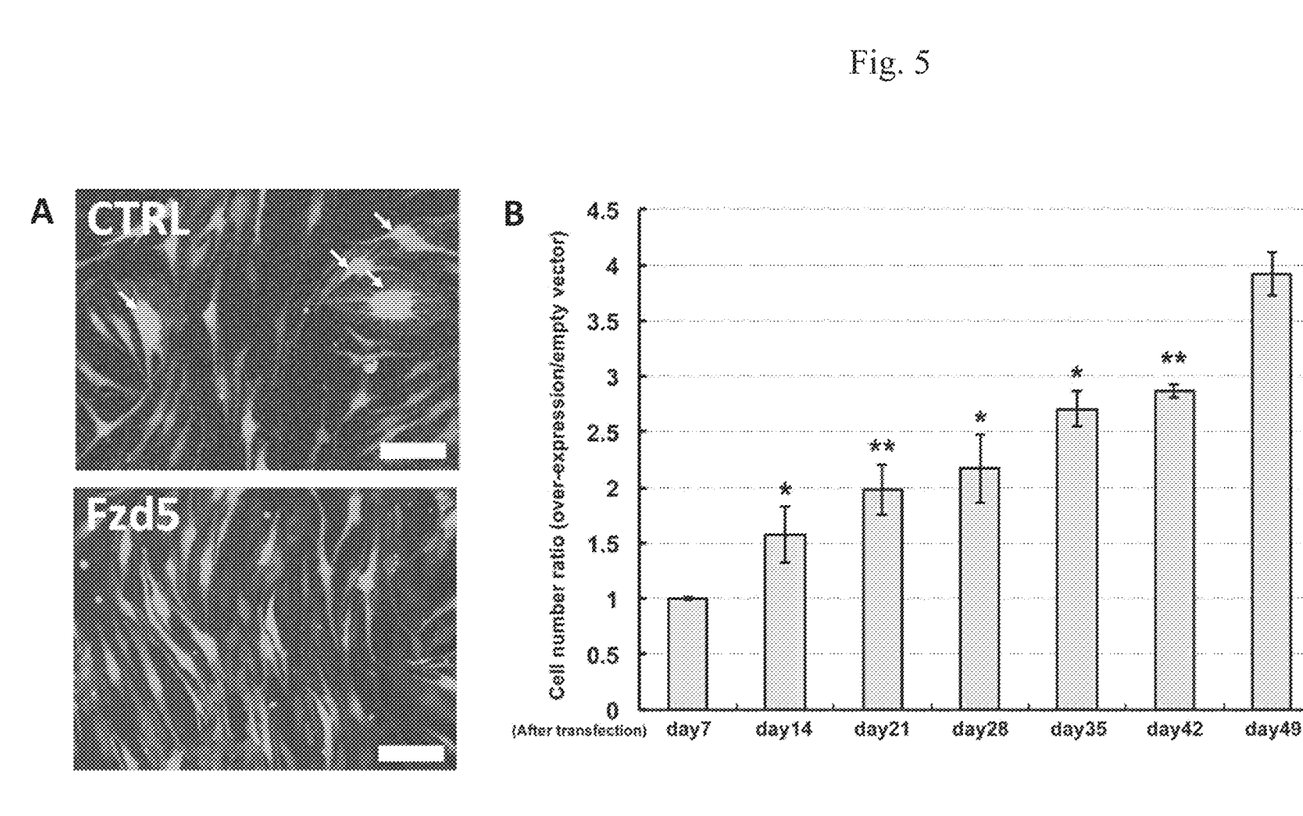
FIG. 5 shows photographs and graphs which indicate that forced expression of Fzd5 incudes the undifferentiated nature of RECs.

Next, while referring to FIG. 5, a discussion will be made about the long-term maintenance of proliferation potency by gain of function of Fzd5.

The full-length cDNA of Fzd5 was forced to be expressed in RECs to cause constitutive expression of Fzd5 mRNA, and the effect thereof on cell functions was confirmed. For this purpose, an expression vector is constructed to carry Fzd5 cDNA and a fluorescent protein GFP (Green Fluorescent Protein) in tandem to thereby allow co-expression of GFP in Fzd5 gene-receiving cells, so that the expression of the introduced gene can be confirmed under a fluorescence microscope.

FIG. 5A shows photographs observed for morphology of GFP-expressing cells under a fluorescence microscope. These images show cell morphology at 28 days after gene transfer in the cell population transformed with Fzd5 cDNA and GFP (Fzd5) as well as the control group transformed with the GFP gene alone (CTRL).

In the control group, there appear many large-sized multipolar cells which are characteristic of cellular aging, as indicated with the arrows in the figure, whereas almost all of the Fzd5-expressing RECs retain their bipolar morphology with small cytoplasm.

FIG. 5B is a graph whose vertical axis plots cell counts of Fzd5-expressing RECs, relative to cell counts in the control group which are set to 1, and whose horizontal axis plots the number of days after gene transfer. RECs forced to express Fzd5 were found to retain their proliferation potency for a long period of time, when compared to the control group.

In view of the above results, Fzd5-mediated stimulation of Wnt signaling would be expected to allow long-term culture amplification in a state maintaining the undifferentiated nature.

Figure 6:
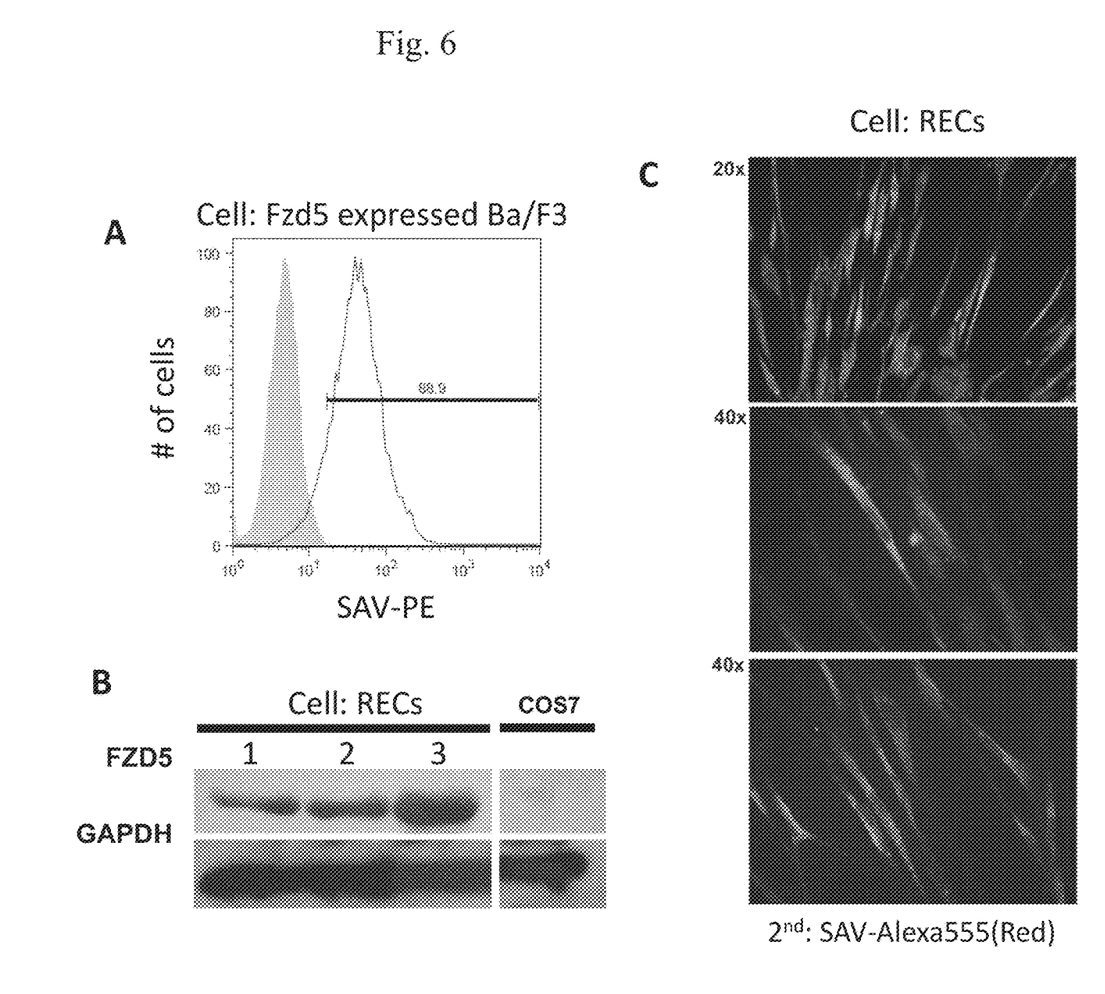
FIG. 6 shows photographs and graphs which indicate the stainability of newly prepared anti-Fzd5 monoclonal antibody.

Subsequently, while referring to FIG. 6, an explanation will be made about the preparation of a novel monoclonal antibody against human Fzd5.

The extracellular region of a human Fzd5 antigen was used as an immunogen to immunize host mice and hybridomas were then prepared in accordance with standard procedures, followed by screening with Ba/F3 cells engineered to express the Fzd5 gene, thereby obtaining a novel anti-Fzd5 monoclonal antibody (clone name: 6F5).

This antibody was used to confirm whether or not the Fzd5 protein was able to be detected by various techniques.

Ba/F3 cells forced to express the extracellular region of Fzd5 were stained with biotin-labeled 6F5 antibody and then fluorescently labeled with streptavidin (SAV)-PE, followed by flow cytometry analysis. FIG. 6A shows a histogram whose horizontal axis plots the fluorescence intensity of PE. The shaded histogram in the figure represents a negative control where an isotype control was added as a primary antibody, while the open histogram represents the PE fluorescence intensity in the sample stained with 6F5. The range indicated with the horizontal bar in the figure represents the range of Fzd5$^+$ cells, while the numerical value represents the positive rate (%).

FIG. 6B shows the results of Western blotting obtained when intracellular proteins were prepared from three different clones of RECs and the Fzd5 protein was detected using 6F5 as a primary antibody. For use as a negative control, intracellular proteins were prepared from the monkey kidney-derived cell line COS7.

FIG. 6C shows images obtained when REC cells were stained with 6F5-biotin as a primary antibody and then fluorescently labeled with streptavidin (SAV)-Alexa 555, followed by observation under a fluorescence microscope. The anti-Fzd5 antibody (6F5) was found to be available for use in all of flow cytometry, Western blotting and immunofluorescent staining.

Figure 7:
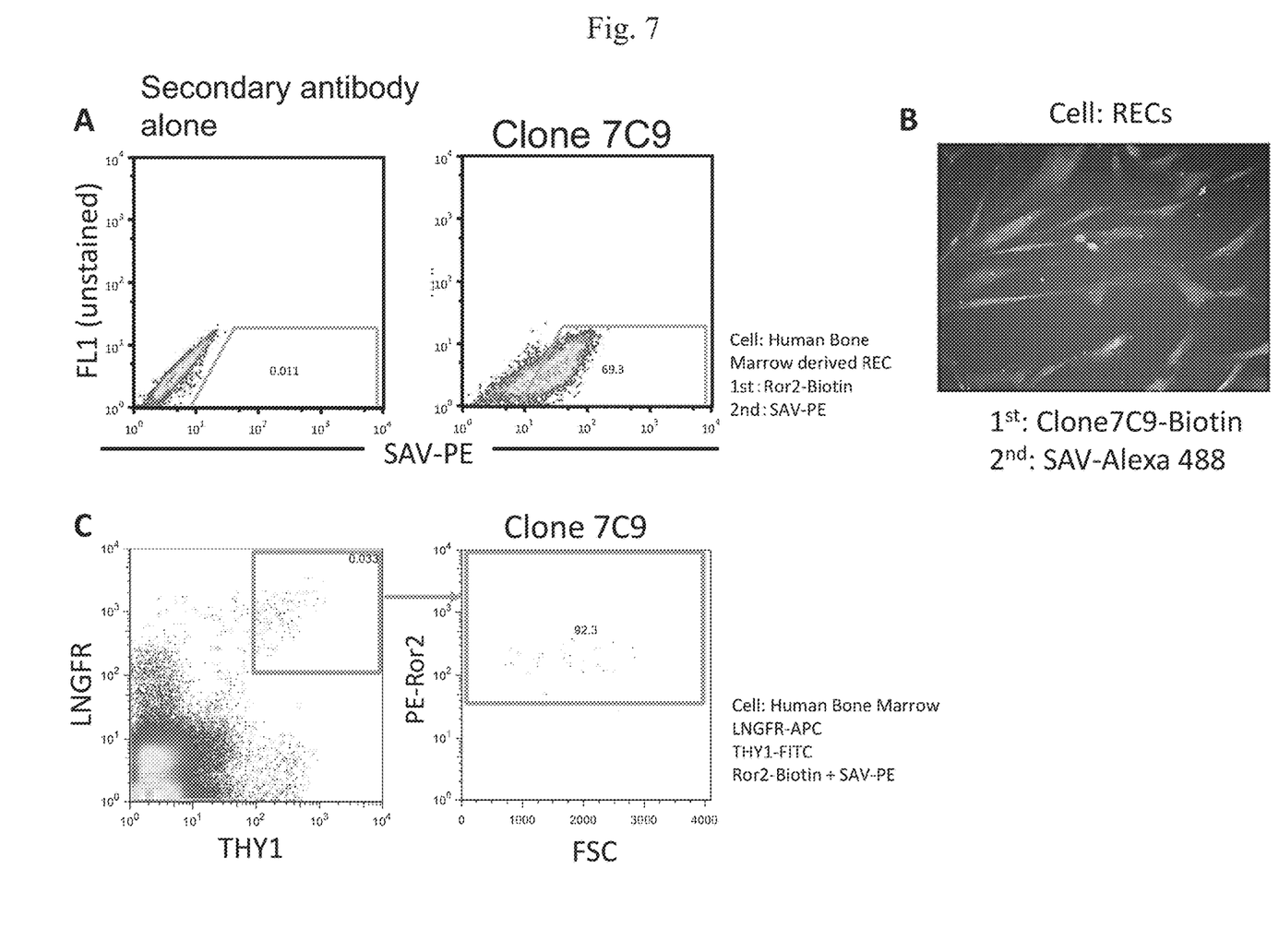
FIG. 7 shows photographs and figures which indicate the stainability of newly prepared anti-Ror2 monoclonal antibody.

Next, while referring to FIG. 7, an explanation will be made about the preparation of a novel monoclonal antibody against a human Ror2 antigen.

A human Ror2 antigen was used as an immunogen to newly prepare an anti-Ror2 antibody (clone name: 7C9).

FIG. 7A shows the results obtained when RECs were stained with 7C9-biotin as a primary antibody and then labeled with SAV-PE, followed by flow cytometry to detect PE fluorescence. A sample prepared by adding an isotype control antibody as a primary antibody is used as a negative control. FIG. 7A is a two-dimensional dot plot whose vertical axis plots FITC fluorescence (RECs are all negative because they are not stained) and whose horizontal axis plots PE fluorescence. Compare to the area that are free from PE fluorescence-emitting cells in the negative control group (i.e., the area within the trapezoid in the figure: 0.011%), a Ror2 expressing cell population was found as a PE fluorescence in the sample stained with clone 7C9 (69.3%).

FIG. 7B is an image obtained when RECs were immunostained with 7C9-biotin as a primary antibody and fluorescently labeled with streptavidin-Alexa 488, and then observed for expression of the Ror2 protein under a fluorescence microscope. Most of these RECs were confirmed to express the Ror2 protein.

FIG. 7C shows the results obtained when fresh bone marrow cells were triple stained with LNGFR-APC, Thy1-FITC and Ror2-PE (monoclonal antibodies against their respective antigens), followed by flow cytometry analysis. The left panel shows a figure whose vertical axis plots LNGFR expression and whose horizontal axis plots Thy1 expression, and the boxed area represents a LNGFR$^+$ Thy1$^+$ cell population containing human MSCs with high frequency. The right figure shows the LNGFR$^+$ Thy1$^+$ cell population extracted alone. The horizontal axis plots FSC serving as an indicator for cell size, while the vertical axis plots PE fluorescence from anti-Ror2-biotin antibody (7C9) labeled with SAV-PE. The boxed area represents the Ror2-positive area determined on the basis of the negative control, and the numerical value represents the positive rate (%). In the case of using clone 7C9, 92.3% of LNGFR$^+$ Thy1$^+$ cells are Ror2-positive; and hence clone 7C9 can be used as a selection marker for MSCs to replace LNGFR Thy1.

Using the newly prepared anti-Ror2 monoclonal antibody, the Ror2 protein can be detected and quantified by flow cytometry and immunofluorescent staining (FIGS. 7A and 7B).

Furthermore, the newly prepared anti-Ror2 can also be used as a marker for MSCs contained in bone marrow (FIG. 7C).

Figure 8:
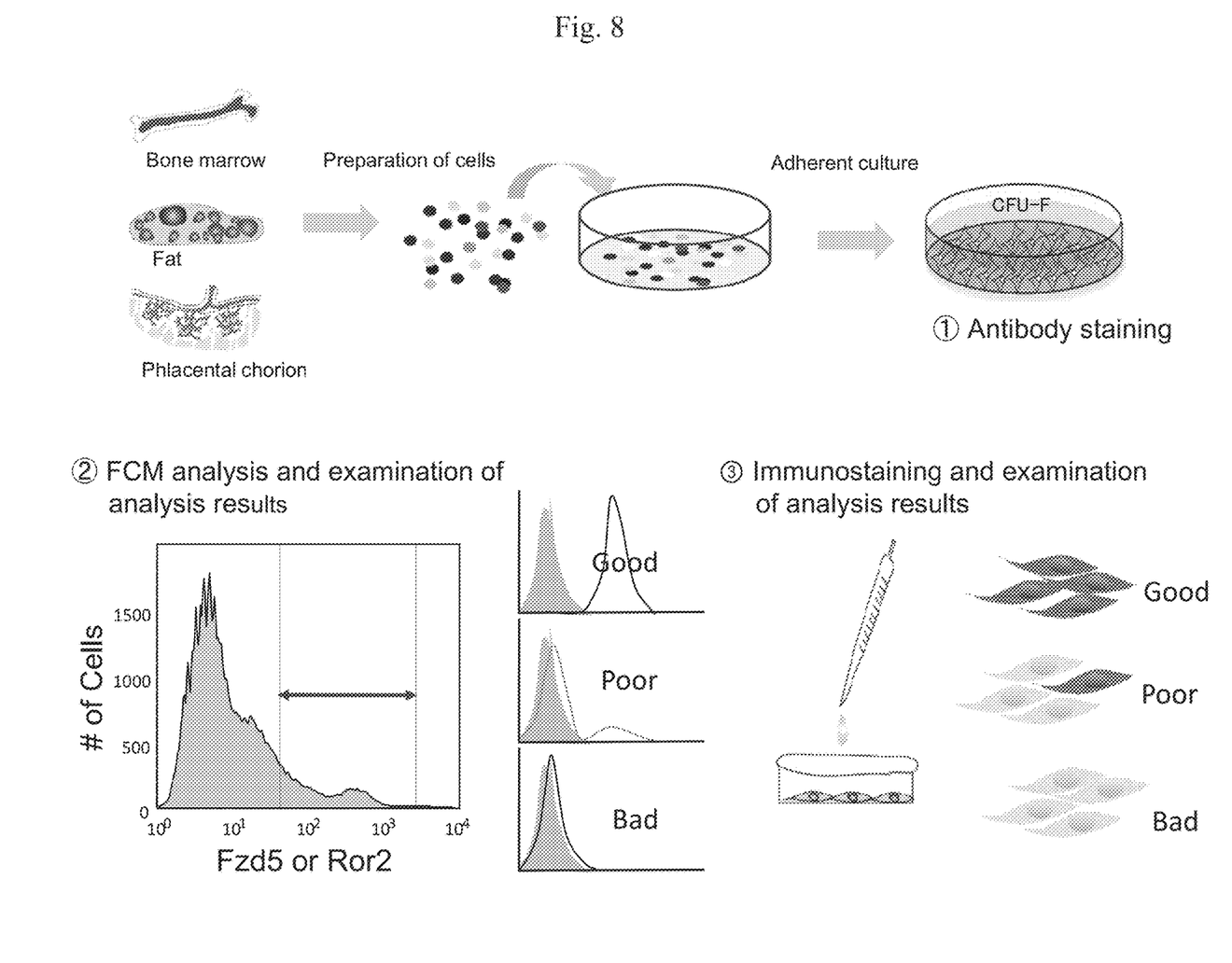
FIG. 8 shows a schematic diagram for quality evaluation of cultured MSCs using REC-specific antibody.

Next, while referring to FIG. 8, an explanation will be made about the procedures for cell quality evaluation using anti-Ror2 antibody or anti-Fzd5 antibody.

Human MSCs cultured in standard adherent culture (or subcultured RECs) are collected and stained with REC-specific monoclonal antibody (anti-Ror2 antibody or anti-Fzd5 antibody).

The frequency (% content) of positive cells is measured by flow cytometry. Alternatively, the frequency (% content) of positive cells may be measured under a fluorescence microscope, instead. These measurements allow quantification of how many RECs are contained in the cell population, which in turn allows evaluation of cell quality, i.e., evaluation of what degree of differentiation, proliferation and migration potency is possessed by the target MSCs. According to the experiments made by the inventors, the Ror2-positive rate of RECs was 72%±8.9% averaged from five lots. Thus, for example, the lowest value, i.e., at least 63% or at least 65% may be used as a reference value for acceptability determination.

INDUSTRIAL APPLICABILITY

The present invention enables the provision of a technique for efficient isolation and culture of human mesenchymal stem cells available for use in the treatment of systemic diseases, and also enables quality evaluation on which to determine whether or not the resulting cell population is suitable for transplantation and/or exerts efficacy.

Among newly prepared monoclonal antibodies showing stainability specific to high purity mesenchymal stem cells, candidates suitable for cell isolation can be provided as reagents for isolation of mesenchymal stem cells by being immobilized on magnetic nanoparticles. Moreover, as reagents for cell evaluation to test the quality of the isolated mesenchymal stem cells, fluorescent substance-labeled antibodies or cell staining reagents can be provided for practical use.

Mesenchymal stem cells are not only used as materials for biomaterials, as previously known, but also can be expected to have various applications by taking advantage of their pluripotency, as exemplified by administration to myasthenia gravis, chronic rheumatism and other diseases, as well as co-transplantation as supporting cells to provide a tissue scaffold (niche) for cell therapy required for treatment of severe diseases including spinal cord injury, hart and vascular failure, chronic liver failure and so on. In particular, the use of RECs retaining their migration potency would be expected to provide a therapeutic effect never seen before when applied to metabolic diseases such as systemic bone and cartilage diseases including hypophosphotasia, for which no therapy has been found, as well as GVHD and all other diseases whose treatment requires administration via the intravenous route.

The invention claimed is:

1. A method for selecting and isolating proliferating human mesenchmal stem cells, which comprises:
  a step 1 where from a cell population containing primary human tissue-derived mesenchymal stem cells, rapidly proliferating human mesenchymal stem cells which are $Ror2^{31}$ cells are single-cell cultured on a culture vessel surface to produce a cell population from said single-cell; and
  a step 2 where the abundance ratio of cells expressing Ror2 collected from the cell population obtained in the step 1 is quantified and
  a step 3 selecting and isolating only the cell population to be at least 63% $Ror2^-$.

2. The method according to claim 1, wherein the cells expressing Ror2 are quantified by immunostaining.

3. The method according to claim 1, wherein the cells expressing Ror2 are quantified by using anti-Ror2 monoclonal antibody.

4. The method according to claim 1, wherein the cells expressing mRNA of Ror2 are quantified by quantitative PCR.

5. The method according to claim 1, wherein the step 1 comprises sorting $Ror2^-$ cells by analyzing cells stained with anti-Ror2 monoclonal antibody by FCM.

6. The method according to claim 5, wherein the sorting comprises seeding the $Ror2^-$ cells in wells of a multi-well culture plate and then isolating and selecting the cells in each well reaching confluence upon culture.

7. The method of claim 1, wherein said percentage is at least 65%.

* * * * *

UNITED STATES PATENT AND TRADEMARK OFFICE
CERTIFICATE OF CORRECTION

PATENT NO. : 11,441,123 B2
APPLICATION NO. : 17/190192
DATED : September 13, 2022
INVENTOR(S) : Yumi Iyoku et al.

It is certified that error appears in the above-identified patent and that said Letters Patent is hereby corrected as shown below:

In the Claims

In Claim 1, at Column 13, Line 16:
Please change "mesenchmal" to --mesenchymal--.

In Claim 1, at Column 13, Lines 18-19:
Please change "stem cells, rapidly proliferating" to --stem cells, proliferating--.

In Claim 1, at Column 13, Line 20:
Please change "Ror2$^{31}$" to --Ror2$^{+}$--.

In Claim 1, at Column 14, Line 5:
Please change "Ror2$^{-}$" to --Ror2$^{+}$--.

In Claim 5, at Column 14, Line 14:
Please change "Ror2$^{-}$" to --Ror2$^{+}$--.

In Claim 6, at Column 14, Line 17:
Please change "Ror2$^{-}$" to --Ror2$^{+}$--.

Signed and Sealed this
Sixteenth Day of April, 2024

Katherine Kelly Vidal
*Director of the United States Patent and Trademark Office*